US009241868B2

(12) United States Patent
Wardle et al.

(10) Patent No.: US 9,241,868 B2

(45) Date of Patent: Jan. 26, 2016

(54) ADJUSTABLE AND REUSABLE EAR ACUPRESSURE DEVICE

(71) Applicants: Kacey Wardle, Brighton, CO (US); Kathy Wardle, Brighton, CO (US)

(72) Inventors: Kacey Wardle, Brighton, CO (US); Kathy Wardle, Brighton, CO (US)

(*) Notice: Subject to any disclaimer, the term of this patent is extended or adjusted under 35 U.S.C. 154(b) by 143 days.

(21) Appl. No.: 13/942,433

(22) Filed: Jul. 15, 2013

(65) Prior Publication Data

US 2015/0018870 A1 Jan. 15, 2015

(51) Int. Cl.
*A61B 17/00* (2006.01)
*A61H 39/04* (2006.01)

(52) U.S. Cl.
CPC ............ *A61H 39/04* (2013.01); *A61H 2201/10* (2013.01); *A61H 2201/165* (2013.01); *A61H 2205/027* (2013.01)

(58) Field of Classification Search
CPC ............ A61H 39/04; A61H 2205/027; A61N 2005/0605; A61N 5/0619
USPC .................................. 606/204; 63/14.1–14.8
See application file for complete search history.

(56) References Cited

U.S. PATENT DOCUMENTS 1,576,372 A * 3/1926 Shea .............................. 63/14.2
4,282,721 A * 8/1981 Roach et al. ................... 63/14.1
4,319,574 A 3/1982 Sun et al.
4,827,738 A * 5/1989 Rothal ........................... 63/14.1
5,247,946 A 9/1993 Holder
5,339,656 A 8/1994 Hieber
6,458,146 B1 * 10/2002 Kramer ......................... 606/204
2008/0310666 A1 * 12/2008 Wengreen .............. H04R 1/026 381/381
2010/0331660 A1 * 12/2010 Wada et al. ................... 600/382
2012/0271345 A1 * 10/2012 Torres ........................... 606/204

FOREIGN PATENT DOCUMENTS

JP 2012-255822 A * 12/2012

OTHER PUBLICATIONS

Robert C. Bright. "Gold and How it Affects the Body." Nov. 23, 2011. pp. 1-3.*
Machine translation from JPO for Terekawa (JP 2012-255822). Published Dec. 27, 2012.*
Robert C. Bright "Gold and How it Affects the Body." Published Nov. 23, 20114. pp. 1-3.*
"The Aculief Mission" located at http://www.aculief.com/pages/about-us, Jul. 1, 2013, 1 pp.

* cited by examiner

*Primary Examiner* — Katherine M Shi
(74) *Attorney, Agent, or Firm* — James A. Sheridan; Sheridan Law, LLC

(57) ABSTRACT

The disclosure provides a reusable, adjustable acupressure device for stimulating an acupuncture point, or acupoint, on the outer ear of a wearer. In one embodiment, the device includes a structural curvature that is adjustably configured to mount to the helix of the external human ear and a bead protruding from the structural curvature. The bead is configured to apply pressure to a select acupoint located on the ear. The device provides the ability for a wearer to stably and reliably stimulate the select acupoint in a manner that is both comfortable and repeatable.
Other embodiments are also disclosed.

19 Claims, 4 Drawing Sheets

ADJUSTABLE AND REUSABLE EAR ACUPRESSURE DEVICE

BACKGROUND

The ear has long-been a vehicle for self-healing, beginning with Chinese acupuncturists in 500 BC, as documented in the *Yellow Emperor's Classic of Internal Medicine*. Today, the benefits of auriculotherapy, or ear acupressure, are increasingly recognized in western self-care practices.

Ear acupressure stimulates the nerve connections between the ear and the central nervous system. Applying pressure to defined points on the external or outer ear triggers nerve impulses between those points and the brain, thereby communicating powerful healing messages to the organ or system in which the health problem manifests.

The auricular acupuncture point, or acupoint, Shenmen is located at the apex of the triangular fossa of the external ear. The point Shenmen is one of the most recognized ear points and is indicated primarily for clarity and balance as well as relief of common ailments such as insomnia, anxiety, depression, and stress.

Current mechanisms for applying sustained pressure to the point Shenmen involve using an adhesive such as medical tape to secure a small ball, tack, magnet, or seed to the point Shenmen. These methods are inconvenient, difficult to employ without a trained specialist, and not amenable to reuse.

The increased popularity of ear acupressure and, more particularly, acupressure involving stimulation of the point Shenmen has created a need for improved ear acupressure methods and apparatus that provide a comfortable fit for most ears in a repeatable, nonintrusive, durable, and reusable manner.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides an acupressure device. The device includes a structural curvature having proximal and distal ends and being configured to mount to the helix of the external human ear. This embodiment also includes a bead protruding from the proximal end of the structural curvature. The bead is configured to apply pressure to an acupuncture point located on the external human ear.

Another embodiment provides a reusable acupressure device that includes a stimulating bead attached to a proximate end of a structural curvature. The stimulating bead and the structural curvature are each configured to press the bead to the triangular fossa of the external ear when the structural curvature is mounted to the helix of the external ear of a wearer.

Yet another embodiment provides a device for treating physiological disorders of the human body by applying pressure to an acupuncture point located on the outer ear of a wearer. The device includes a mounting having a curving structure configured to adjustably wrap around the helix of the outer ear of the wearer. The device also includes a stimulating bead protruding from a proximal end of the mounting. The stimulating bead is configured to abut and apply pressure to the acupuncture point when the mounting is wrapped around the helix of the outer ear of the wearer.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the invention. However, embodiments may be implemented in many different forms and should not be construed as being limited to the embodiments set forth herein. The following detailed description is, therefore, not to be taken in a limiting sense.

Figure 1:
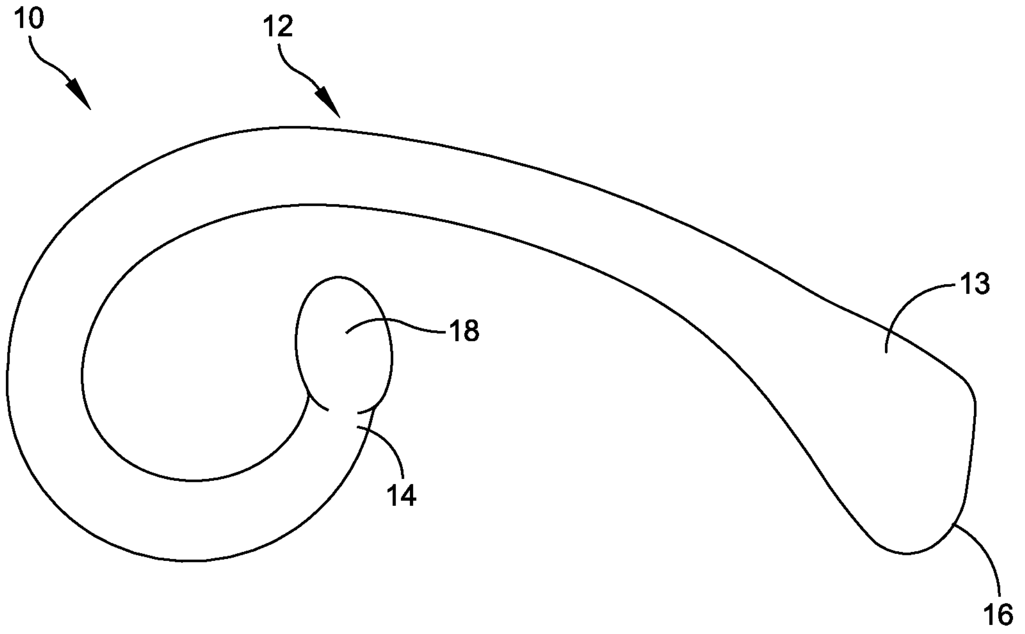
FIG. 1 illustrates a top plan view of a reusable acupressure device according to one embodiment of the present invention.
Figure 2:
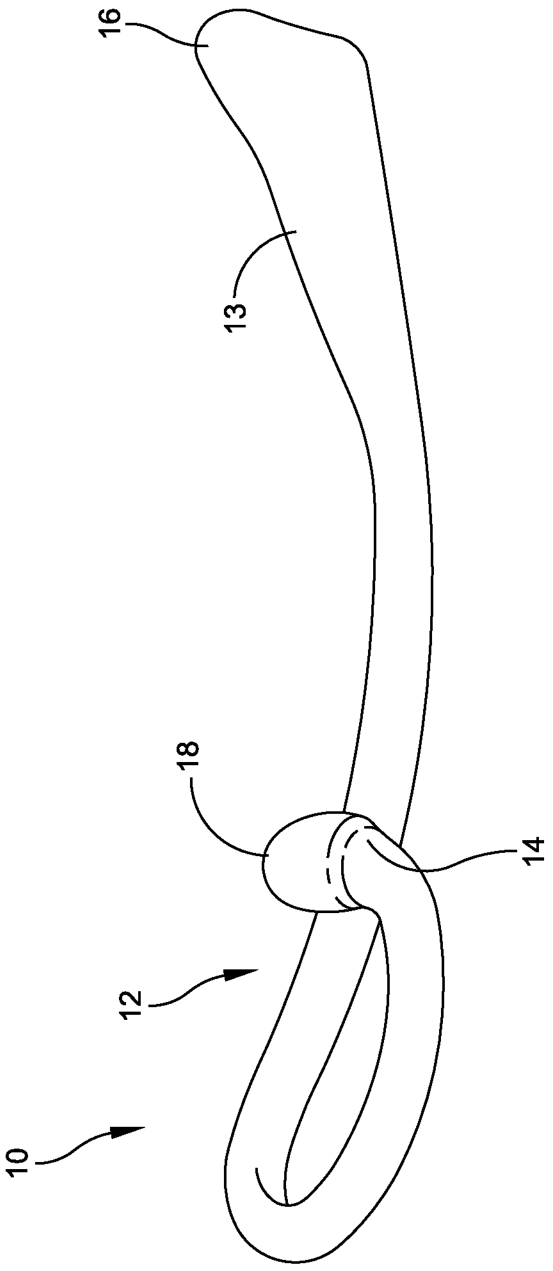
FIG. 2 illustrates a front elevation view of the reusable acupressure device of FIG. 1.
Figure 3:
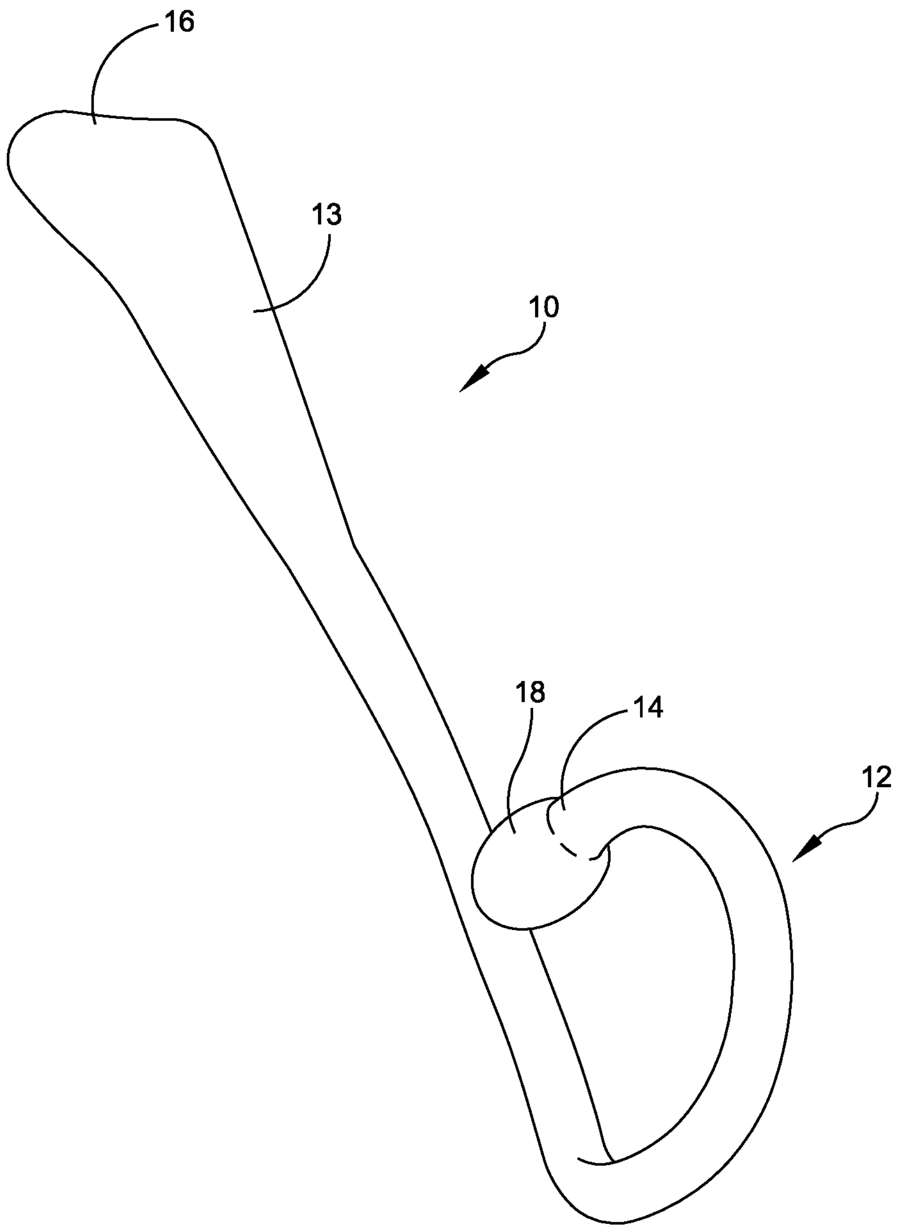
FIG. 3 illustrates a perspective view of the reusable acupressure device of FIG. 1.
Figure 4:
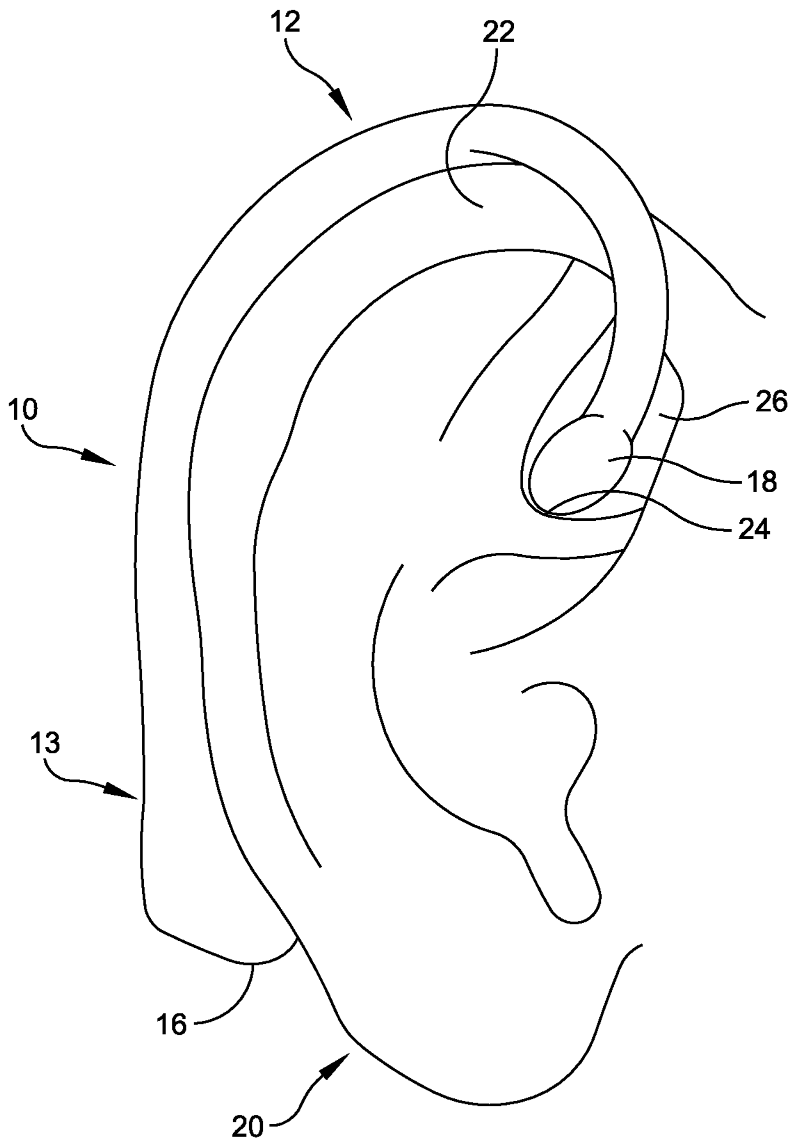
FIG. 4 illustrates the reusable acupressure device of FIG. 1 as mounted upon a human ear.

FIGS. 1-3 illustrate top, side, and perspective views of a reusable acupressure device 10 according to one embodiment of the present invention, respectively. The reusable acupressure device 10 includes a structural curvature 12 having a proximal end 14 that terminates near a wearer's ear 20, as shown in FIG. 4, discussed in detail below, and an opposing distal end 16. A stimulating bead 18 protrudes from the proximal end 14.

FIG. 4 illustrates the reusable acupressure device 10 as mounted upon the outer human ear 20. The reusable acupressure device 10 employs the natural features of the outer ear 20 to provide for comfortable and repeatable mounting of the device 10. These natural features include a helix 22 and a triangular fossa 26.

In this embodiment, the structural curvature 12 of the acupressure device 10 is configured to wrap around the helix 22 of the outer ear 20 such that the stimulating bead 18 at the proximal end 14 of the device 10 abuts and applies pressure to an apex 24 of the triangular fossa 26. This particular area of the ear 20 is known as the auricular acupoint Shenmen, a recognized ear point indicated primarily for clarity and balance as well as relief of common ailments such as insomnia, anxiety, depression, and stress. The particular wrapping of the structural curvature 12 around the helix 22 in a Fibonacci-like spiral stabilizes the stimulating bead 18 at the point Shenmen, providing sustained pressure for effectiveness. The structural curvature 12 defines a three-dimensional spiral extending from an initial plane at the distal end to a second plane, different from the initial plane, adjacent the proximal end.

The stimulating bead 18 may have any appropriate size, shape, and/or configuration to provide proper stimulation of the point Shenmen. For example, adding or removing thickness to or from the stimulating bead 18 controls the pressure upon the acupoint for different effects. In other embodiments, the stimulating bead 18 may incorporate additional stimulating materials, such as, for instance, magnets, tacks, seeds, and/or gold balls.

In addition, the structural curvature 12 may take any appropriate size, shape, and/or configuration to allow for comfortable, stable mounting upon the ear 20. For instance, the design of structural curvature 12, either in configuration, composition, or otherwise, may provide a flexible or malleable structure that can be adjusted to a particular fit. In this embodiment, a distal portion of the curvature has been enlarged to form a comfort grip 13 to cushion or pad the back of the ear 20 when the structural curvature 12 is wrapped around the helix 22 of the ear 20. In other embodiments, the structural curvature 12 may be configured as necessary to accommodate different materials, sizes, cushion levels, and attachment sites on the ear 20.

While the acupressure device 10 is configured to apply pressure to the point Shenmen at the apex 24 of the triangular fossa 26 of the ear 20, other embodiments may be configured to stimulate and/or apply pressure to other acupoints located on the outer ear 20. For example, targeting other points on the ear 20 may require different components, component sizes, curvatures, and/or attachment points.

The reusable acupressure device 10 may be formed of one or more appropriate materials, including metals such as but not limited to stainless steel, copper, gold, sterling silver, platinum, titanium, and/or palladium. Alternatively, the device 10 may be formed of an appropriate plastic or polymer such as an injectable silicone. In some embodiments, the device 10 may be formed of a uniform material. In others, the structural curvature 12 may be formed from a different material than the stimulating bead 18. Still another material may be employed to form the grip 13, discussed above.

Classical Chinese Medicine theorizes that different materials result in different physiological effects. As a result, the one or more materials used to manufacture alternative embodiments of the acupressure device 10 may be selected based on the physiological effects sought. For example, metals such as gold or copper will be stimulating, while metals such as stainless steel or sterling silver will provide a sedative effect.

Embodiments of the acupressure device 10 may be manufactured in any appropriate manner, dependent upon the material selected. For example, embodiments of the device 10 may be injection molded in a single piece or in two or more pieces that are later assembled. Other embodiments of the device 10 may be machined from metal or printed via a three-dimensional printer.

The elegant configuration of the acupressure device 10 allows a wearer to use and reuse the device 10 in a manner that is comfortable, stable, and reliably repeatable. Moreover, the flexible nature of the structural curvature 12 may be adjusted to fit multiple ear sizes. Rather than depending on a trained specialist for stimulation of the Shenmen or other acupoints on the ear 20 using disposable tacks, seeds, balls, or magnets that must be carefully adhered to the acupoint, a wearer may comfortably employ the device 10 to meet his/her needs.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. An ear acupressure device comprising:

a structural curvature having a proximal end and a distal end, said structural curvature configured to extend over, and mount to, the helix of the external human ear; and a bead protruding from said proximal end of said structural curvature, said bead configured to apply pressure to an acupuncture point located on the external human ear and inward of the helix of the external human ear;

said structural curvature defining a three-dimensional spiral extending from an initial plane at the distal end to a second plane, different from the initial plane, adjacent the proximal end, and the three-dimensional spiral configured to position said bead out of the initial plane of the distal end of the structural curvature so as to cause sustained pressure to the acupuncture point located on the external human ear;

wherein said bead is configured to provide a desired mount of pressure against the triangular fossa of the external human ear.

2. The ear acupressure device of claim 1, wherein said structural curvature is adjustable.

3. The ear acupressure device of claim 1, wherein said structural curvature is formed of a first material and said bead is formed of a second material.

4. The ear acupressure device of claim 3, wherein said first material and said second material are identical.

5. The ear acupressure device of claim 3, wherein said first material comprises a first metal or a first plastic and said second material comprises a second metal or a second plastic.

6. The ear acupressure device of claim 5, wherein said first metal comprises steel, copper, gold, sterling silver, titanium, palladium, or platinum and said second metal comprises steel, copper, gold, sterling silver, titanium, palladium, or platinum.

7. The ear acupressure device of claim 5, wherein said first plastic comprises an injectable polymer or a printable polymer and said second plastic comprises an injectable polymer or a printable polymer.

8. The ear acupressure device of claim 1, wherein said structural curvature has a first thickness and said bead has a second thickness.

9. The ear acupressure device of claim 8, wherein said first thickness is based on a desired fit of said structural curvature around the helix of the external human ear.

10. The ear acupressure device of claim 8, wherein said second thickness is based on a desired strength of said pressure applied to the acupuncture point.

11. A reusable acupressure device comprising: a stimulating bead attached to a proximate end of a structural curvature, said stimulating bead and said structural curvature each configured to press said bead to the triangular fossa of the external ear of a wearer when said structural curvature is mounted to the helix of the external ear of the wearer, said structural curvature defining a three-dimensional spiral extending from an initial plane at a distal end to a plane, different from the initial plane, adjacent a proximal end, and the three-dimensional spiral configured to extend over, and mount to, the helix of the human ear, and configured to position said bead out of the initial plane of the distal end of the structural curvature so as to cause sustained pressure to the acupuncture point located on the external human ear, wherein said bead is configured to provide a desired mount of pressure against the triangular fossa of the external ear of the wearer.

12. The acupressure device of claim 11, wherein said structural curvature is formed of a first material and said bead is formed of a second material.

13. The acupressure device of claim 12, wherein said first material and said second material are identical.

14. The acupressure device of claim 12, wherein said first material comprises a first metal or a first plastic and said second material comprises a second metal or a second plastic.

15. The acupressure device of claim 14, wherein said first metal comprises steel, copper, gold, sterling silver, titanium, palladium, or platinum and said first plastic comprises an injectable polymer or a printable polymer.

16. The acupressure device of claim 14, wherein said second metal comprises steel, copper, gold, sterling silver, titanium, palladium, or platinum and said second plastic comprises an injectable polymer or a printable polymer.

17. The acupressure device of claim 11, wherein said structural curvature has s first thickness and said stimulating bead has a second thickness.

18. A device for treating physiological disorders of the human body by applying pressure to an acupuncture point located inward of the helix of the external human ear and on the outer ear of a wearer, said device comprising:

a mounting comprising a curving structure configured to extend over, and adjustably wrap around, the helix of the outer ear of the wearer; and a stimulating bead protruding from a proximal end of said mounting, said stimulating bead configured to abut and apply pressure to the acupuncture point located inward of the helix of the external human ear when said mounting is wrapped around the helix of the outer ear of the wearer;

said structural curvature defining a three-dimensional spiral extending from an initial plane at a distal end to a plane, different from the initial plane, adjacent a proximal end, and the three-dimensional spiral configured to position said bead out of the initial plane of the distal end of the structural curvature so as to cause sustained pressure to the acupuncture point located on the external human ear;

wherein said bead is configured to provide a desired mount of pressure against the triangular fossa of the external ear of the wearer.

19. The device of claim 18, wherein said device is reusable.

* * * * *